United States Patent
Bedoukian et al.

(10) Patent No.: US 7,932,410 B2
(45) Date of Patent: Apr. 26, 2011

(54) PRODUCTION OF PHEROMONES AND FRAGRANCES FROM SUBSTITUTED AND UNSUBSTITUTED 1-ALKEN-3YL ALKYLATES

(75) Inventors: Robert H. Bedoukian, West Redding, CT (US); Linda C. Passaro, Bethel, CT (US)

(73) Assignee: Bedoukian Research, Inc., Danbury, CT (US)

( * ) Notice: Subject to any disclaimer, the term of this patent is extended or adjusted under 35 U.S.C. 154(b) by 244 days.

(21) Appl. No.: 12/290,603

(22) Filed: Oct. 31, 2008

(65) Prior Publication Data

US 2010/0113837 A1    May 6, 2010

(51) Int. Cl.
*C07F 3/02* (2006.01)
*C07C 27/00* (2006.01)
*C07C 67/02* (2006.01)

(52) U.S. Cl. .......... 556/96; 568/874; 568/876; 560/129; 560/261

(58) Field of Classification Search .................. None
See application file for complete search history.

(56) References Cited

U.S. PATENT DOCUMENTS

| | | | |
|---|---|---|---|
| 4,844,916 A | 7/1989 | Ogawa et al. | 424/409 |
| 4,912,253 A | 3/1990 | Fukumoto et al. | 560/261 |

OTHER PUBLICATIONS

Paintner, F. F. et al, Toward the synthesis of tetrodecamycin: asymmetric synthesis of a direct precursor of the C6-C18 trans-decalin portion, 2003, Tetrahedron Letters, 44, pp. 2549-2552 (4 pages).*
Silverman, G., Handbook of Grignard Reagents, 1996, Dekker Publishing, p. 591 (3 pages).*
Marshall, J.A., Sn2' Addtions of Organocopper Reagents to Vinyloxiranes, 1989, Chem. Rev., vol. 89, pp. 1503-1511.*
Magid, R.M., Nucleophilic and Organometallic Displacement Reactions of Allylic Compounds: stero- and regiochemistry, 1980, Tetrahedron, vol. 36, pp. 1901-1930.*
Henne et al., J. Am. Chem. Soc., 63, 3474-3476 (1941).
Blackvall et al.,J. Am. Chem. Soc., 112, 6615-6621 (!990).
Vig et al., J. Indian Chem. Soc., 66, 233-235 (!989).
Weisner et al., Chem. Ind., 15, 627-628 (1980).
Ishmuratov et al., Russian Chem., Bull., 46, 1035-1037 (1997).
Handbook of Grignard Reagents, Gary S. Silverman et al., p. 591, Apr. 25, 1996; Deeker Publisher.

* cited by examiner

*Primary Examiner* — Jafar Parsa
*Assistant Examiner* — Yate K Cutliff
(74) *Attorney, Agent, or Firm* — Ohlandt, Greeley, Ruggiero & Perle, LLP; George W. Rauchfuss, Jr.

(57) ABSTRACT

Compounds of the formula (I)

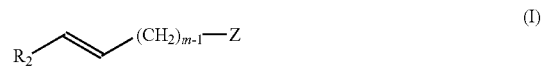

wherein $R_2$ is a branched or unbranched, saturated or ethylenically mono or di unsaturated aliphatic radical, Z is —$CH_2OH$, —$CH_2OAc$ or —CHO, m is a whole positive integer of one or more, and Ac is an acetyl group are synthesized by a process wherein a 1-alken-3-yl alkylate, is reacted with a halo alkanol Grignard reagent.

20 Claims, No Drawings

US 7,932,410 B2

PRODUCTION OF PHEROMONES AND FRAGRANCES FROM SUBSTITUTED AND UNSUBSTITUTED 1-ALKEN-3YL ALKYLATES

FIELD OF THE INVENTION

The invention relates to an improved method for the synthesis of compounds that are pheromones and fragrances from substituted and unsubstituted 1-alken-3-yl alkylate compounds and particularly to the production of such pheromones and fragrances that have improved yields and more particularly, greater trans isomeric content.

BACKGROUND OF THE INVENTION

In March 2007 the presence of the light brown apple moth (LBAM), *Epiphyas postvittana*, was confirmed in California by the U.S. Department of Agriculture Animal and Plant Health Inspection Service (APHIS). It was first found in Alameda County and as of July 2007 has been found in eight San Francisco Bay area counties along with Monterey, Santa Cruz, and Los Angeles counties. APHIS issued a Federal Domestic Quarantine order on May 2, 2007, with restrictions on interstate shipment of plant material, and the California Department of Food and Agriculture (CDFA) issued a State Interior Quarantine order restricting intrastate shipment of plant material from counties where light brown apple moth is known to occur. The LBAM larvae cause damage to the leaves and fruit of apples, pears, grapes, citrus varieties, black and red currants, kiwifruit, hops, red and white clovers, lucerne, tree lupin, plantain, tutu, gorse, chrysanthemum, michaelmas daisy and other flowering plants, shrubs, especially acacias and conifers in the young stages of growth. The moth may have 2-4 generations annually in a temperate climate. Eggs are laid in clusters of 3 to 150 on leaves or fruit, which hatch to provide the larvae. To combat LBAM the pheromone 11E-tetradecen-1-yl acetate has been favorably employed.

The peach twig borer is one of the most significant pests on peach, nectarine, and apricot. The larvae of the overwintering generation emerge during bloom to petal fall and burrow into developing shoots. When populations are high these larvae can cause substantial damage to young trees. The first adults are usually detected during mid- to late May. Most economic damage results during the summer when larvae of summer generations attack the fruit. Insecticides are currently the most effective control tactic. Pre-bloom to petal fall sprays that target the young larvae provide the best control of the peach twig borer. Peach twig borer can damage stone fruits by feeding in shoots and causing shoot strikes, or by feeding directly on the fruit. Shoot damage is most severe on the vigorous growth of young, developing trees because feeding kills the terminal growth and can result in undesirable lateral branching. As fruit matures, it becomes highly susceptible to attack with damage most likely to occur from color break to harvest. Twig borer larvae generally enter fruit at the stem end or along the suture and usually feed just under the skin. To combat this insect the pheromone, 5E-decenyl acetate, has been employed.

The compound 8E 10,E-dodecadien-1-yl acetate has been found to be useful against destructive insects such as red pine shoot borer, hickory shuckworm, pea moth, chestnut tortrix, gorse pod moth, Chinese tortrix as well as other Lepidoptera. The corresponding alcohol, 8E, 10E-dodecadien-1-ol, has been found to be especially useful against the codling moth insect.

The black-headed budworm is the most significant defoliator of the coastal spruce-hemlock forests in the Western United States and Alaska. This insect is particularly common in southwest Alaska, the Prince William Sound area, and throughout southeast Alaska. The black-headed budworm's preferred host is western hemlock, but Sitka spruce and mountain hemlock are also frequently fed upon. The black-headed budworm (*Acleris gloverana* Walsingham) is a native insect of western North America. Until recently this insect was considered one species, *Acleris variana* (Fernald). Taxonomic studies show that various species are probably involved: three western species, *A. gloverana*, and an eastern species, *A. variana*. The range of *A. gloverana* is from northern California and areas in the Rocky Mountain northward into Yukon and Northwest Territories in Canada and southeastern Alaska. The eastern portion of the range of *A. gloverana* may overlap the western portion of the range of *A. variana*, which extends to the Atlantic seaboard. When conditions favor a high population of the black-headed budworm, the larvae cause extensive defoliation of hemlock spruce, and several species of fir trees of all ages may be killed, top-killed, or severely weakened. Widespread outbreaks, sometime covering millions of acres, have occurred periodically in the Pacific Northwest, British Columbia and coastal Alaska. The budworm has often been accompanied or followed by high populations of other defoliators such as the hemlock sawfly and the spruce budworm. An especially useful pheromone against blackheaded budworm is 11E,13-tetradecadienal.

The spruce budworm *Choristoneura fumiferana* (Clemens) is one of the most destructive native insects in the northern spruce and fir forests of the Eastern United States and Canada. Periodic outbreaks of the spruce budworm are a part of the natural cycle of events associated with the maturing of balsam fir. An especially effective pheromone against the spruce budworm is 11E-tetradecenal.

The compounds of this invention, including those pheromones mentioned above will generally have the formula (I)

wherein $R_2$ is a branched or unbranched, saturated, ethylenically or mono or di unsaturated aliphatic radical, Z is —CH$_2$OH, —CH$_2$OAc or —CHO, m is a whole positive integer of one or more, generally from 1 to 20, and Ac is an acetyl group. The unsaturation can be any ethylenic unsaturation. While these compounds are effective pheromones to combat various insects many of the compounds of this formula are also useful as fragrances, such as for example, 5E-octenal.

While these synthetic pheromones and fragrances have been produced using synthesis procedures such as those disclosed in J. Amer. Chem. Soc., Vol. 112, pp 6615-6621 (1999) and U.S. Pat. No. 4,912,253 there is a need for a process to produce such compounds in greater yields. Also there is a need to be able to produce compounds of this type wherein the percentage of trans isomer is increased since the trans isomer of the pheromone compounds mentioned are generally more effective.

SUMMARY OF THE INVENTION

In accordance with this invention any compounds of the formula (I)

wherein $R_2$ is a branched or unbranched, saturated, or ethylenically mono or di unsaturated, aliphatic radical, Z is —$CH_2OH$, —$CH_2OAc$ or —CHO, m is a whole positive integer of one more generally from 1 to 20, and Ac is an acetyl group are synthesized by a process wherein a 1-alken-3-yl alkylate, particularly a substituted and unsubstituted 1-penten-3-yl alkylate compound of the formula (II)

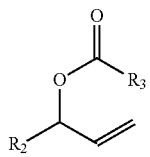

(II)

wherein $R_2$ is a branched or unbranched, saturated, or ethylenically mono or di unsaturated aliphatic radical, and $R_3$ is a branched or unbranched alkyl group of 2 or more carbon atoms, preferably of from 2 to 4 carbon atoms, is reacted with a halo alkanol Grignard reagent of the formula (III)

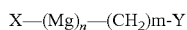

(III)

wherein X is a halogen selected from Cl, Br and I, n is 1, m is a whole positive integer of 1 or more, preferably 1 to 20, and Y is —$O^-Mg^{+2}X^-$, or (—$OR_4$)$_2$ or

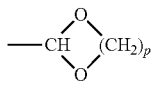

wherein $R_4$ is an alkyl group of from 1 to 4 carbon atoms and p is a whole integer of from 1 to 4 and with the proviso that when Y is (—$OR_4$)$_2$ or

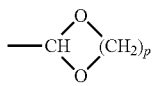

m is 1 or more to produce compounds of formula (I) wherein Z is —$CH_2OH$, and when products of formula (I) wherein Z is $CH_2OAc$ is desired, the product of formula (I) wherein Z is $CH_2OH$ is reacted with any suitable acetylating agent, such as for example an acetyl halide or acetic anhydride and the like, preferably acetic anhydride, and when the product of formula (I) wherein Z is CHO is desired a reactant of formula (III) wherein Y is (—$OR_4$)$_2$ or

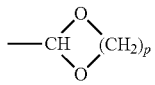

is employed and the resulting reaction product is deprotected to provide the aldehyde (—CHO) group. The reaction of reactants (II) and (III) is generally conducted in the presence of a any suitable copper catalyst, such as for example, including but not limited to $Li_2CuBr_4$, $LiCuBr_2$, copper iodide, copper acetate, copper cyanide, copper (II) triflate, $Li_2CuCl_4$, $LiCuCl_2$, and preferably a copper halide or lithium copper halide catalyst $LiCu(X^2)_2$ wherein $X^2$ is chlorine, bromine, or iodine.

When it is desired that the products of formula (I) have the highest trans isomer amount produced in the reaction of reactants of formulae (II) and (III) then when neither X nor Y in the reactant of formula (III) is bromine $X^2$ is bromine. The presence of bromine in either the reactant of formula (III) or in the lithium copper halide catalyst also generally produces the highest yield of compounds of formula (I) compared to when only the halides Cl or I are present in the reactants and catalyst.

DETAILED DESCRIPTION OF THE INVENTION

Pheromones and fragrances of the formula (I)

(I)

wherein $R_2$ is a branched or unbranched, saturated or ethylenically mono or di unsaturated aliphatic radical, Z is —$CH_2OH$, —$CH_2OAc$ or —CHO, m is a whole positive integer of 1 or more, preferably 2 to 14, and Ac is an acetyl group are synthesized by a process wherein a 1-alken-3-yl alkylate, particularly a substituted and unsubstituted 1-penten-3-yl alkylate compound of the formula (II)

(II)

wherein $R_2$ is a branched or unbranched, saturated, or ethylenically mono or di unsaturated aliphatic radical, and $R_3$ is a branched or unbranched alkyl group of 2 or more carbon atoms, generally from 1 to 20, and preferably from 2 to 4 carbon atoms, is reacted with a halo alkanol Grignard reagent of the formula (III)

(III)

wherein X is a halogen selected from Cl, Br and I, n is 1, m is a whole positive integer of 1 or more, preferably 1 to 20, more preferably 1 to 10 and even more preferably 1 to 4, and Y is —$O^-Mg^{+2}X^-$, or (—$OR_4$)$_2$ or

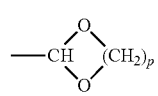

wherein $R_4$ is an alkyl group of from 1 to 4, preferably 1 to 2, carbon atoms and p is a whole integer of from 1 to 4, preferably 2, and with the proviso that when Y is (—$OR_4$)$_2$ or

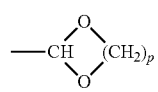

m is 1 to produce compounds of formula (I) wherein Z is —$CH_2OH$, and when products of formula (I) wherein Z is $CH_2OAc$ is desired the product of formula (I) wherein Z is CH$_2$OH is reacted with any suitable acetylating agent, such as for example an acetyl halide or acetic anhydride and the like, preferably acetic anhydride. and when the product of formula (I) wherein Z is CHO is desired the reactant of formula (HI) wherein Y is (—OR$_4$)$_2$ or

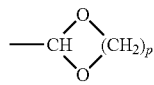

is employed the resulting reaction product is deprotected to provide the aldehyde (—CHO) group.

The reaction of reactants (II) and (III) is conducted in the presence of any suitable copper catalyst, such as for example, including but not limited to Li$_2$CuBr$_4$, LiCuBr$_2$, copper iodide, copper acetate, copper cyanide, copper (II) triflate, Li$_2$CuCl$_4$, LiCuCl$_2$, and preferably a copper halide or lithium copper halide catalyst LiCu (X$^2$)$_2$ wherein X$^2$ is chlorine, bromine, or iodine. When it is desired that the products of formula (I) have the highest trans isomer amount produced in the reaction of reactants of formulae (II) and (III) then when neither X nor Y in reactant of formula (III) is bromine X$^2$ is bromine. The presence of a bromine in either reactant of formula (III) or in the copper catalyst and preferably in a lithium copper halide catalyst also generally produces the highest yield of compounds of formula (I) compared to when only the halides Cl or I are present in the reactants and catalyst. The catalyst is generally employed in an amount of from about 1 to about 10 mole percent based on the halo alkanol Grignard reagent. It has been discovered that use of the catalyst in a mole percent of 4 or more generally produces a higher ratio of trans isomer in the products of formula (I). Preferably the catalyst is added to the reaction vessel with the 1-alken-3-yl alkylate reactant of formula (II) to also improve the yield of trans isomer of the product of formula (I).

It has also been discovered that under equivalent reaction conditions when R$_3$ of reactant of formula (II) is an C$_3$ alkyl group a higher yields of product of formula (I) is generated than when R$_3$ of reactant of formula (II) is an C$_2$ alkyl.

While the reaction may be conducted at any suitable temperature of from about room temperature and above up to about 45° C., it has been determined that employing a reaction temperature of from about 20° C. to about 40° C., and preferably from about 25° C. to about 30° C. generally produces higher amounts of trans isomer in the product than when the reaction is conducted at lower temperatures. Reaction temperatures above about 45° C. are not employed as the catalyst becomes unstable at these higher temperatures.

The reaction of reagent II with reagent III can employ either a two-pot process or a three-pot process. In the two pot process, the alkanol alkoxide reagent of formula III wherein n=0 is made (Pot 1) and added to a mixture of magnesium in an ethereal solvent (Pot 2) to give the reagent of formula III wherein n=1. To this solution is added the copper catalyst followed by the 1-alken-3-yl alkylate of formula II. In the three pot process, the first two steps are performed to produce reagent III, followed by adding the solution of reagent III wherein n=1 to another reaction vessel (Pot 3) containing reagent II, 1-alken-3-yl alkylate, and copper catalyst. It has also been determined that it is generally preferable to conduct the synthesis of this invention as a three pot reaction rather than a two pot reaction, although the latter may be employed. While the reaction of reactant of formula (II) with the reactant of formula (III) may be initiated by either adding reactant (II) to reactant (III) or by adding reactant (III) to reactant (II) it is generally preferred to add reactant (III) to the alkylate reactant (II).

Examples of pheromones which can be used within the scope of the present invention are the following compounds: dodecanyl acetate, 7E-dodecenyl acetate, 8E-dodecenyl acetate, 9E-dodecenyl acetate, 10E-dodecenyl acetate, 11-dodecenyl acetate, 9E,11-dodecadienyl acetate, 11E-tridecenyl acetate, tetradecanyl acetate, 7E-tetradecenyl acetate, 8E-tetradecenyl acetate, 9E-tetradecenyl acetate, 10E-tetradecenyl acetate, 11E-tetradecenyl acetate, 12E-pentadecenyl acetate, hexadecanyl acetate, 11E-hexadecenyl acetate, octadecanyl acetate, 7E,9Z-dodecadienyl acetate, 7E,9E-dodecadienyl acetate, 8E,10E-dodecadienyl acetate, 9E,12Z-dodecadienyl acetate, 4E,7Z-tridecadienyl acetate, 9E,11E-tetradecadienyl acetate, 7E,11Z-hexadecadienyl acetate, 7E,11E-hexadecadienyl acetate, 3E,13Z-octadecadienyl acetate, 3E,13E-octadecadienyl acetate, 6E-nonenol, dodecanol, 11-dodecenol, 7E-dodecenol, 8E-dodecenol, 9E-dodecenol, 9E,11-dodecadienol, 5E,7E-dodecadienol, 8E,10E-dodecadien-1-ol (codlemone, codlure, 8E,10Z-dodecadienol, 7E,9Z-dodecadienol, 5E-tetradecenol, 9E-tetradecenol, 11E-tetradecenol, 14E-methyl-8-hexadecen-1-ol, 10E,12E-hexadecadienol, 10E,12Z-hexadecadienol, dodecanal, tetradecanal, 11E-tetradecanal, 11E,13-tetradecadienal, 8E,10E-tetradecadienal, hexadecanal, 10E-hexadecenal, 11E-hexadecenal, 14E-14-methyl-8-hexadecenal, 10E,12E-hexadecadienal, 10E,12Z-hexadecadienal, octadecanal, and 13E-octadecenal.

The invention is illustrated by, but not limited to, the following synthesis examples.

EXAMPLE 1

Chlorononanol Coupling to 1-Penten-3-yl Isobutyrate

LBAM Monoene Component

11E-Tetradecen-1-yl acetate

Preparation of Chlorononanol Alkoxide:

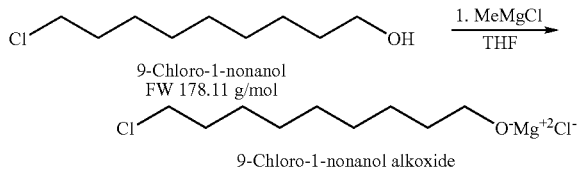

Preparation of Chlorononanol Alkoxide Grignard:

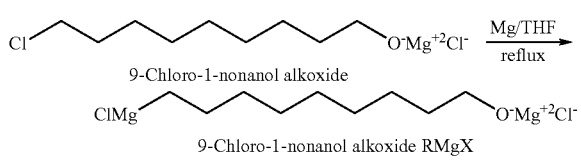

Preparation of 11E-Tetradecen-1-yl Acetate:

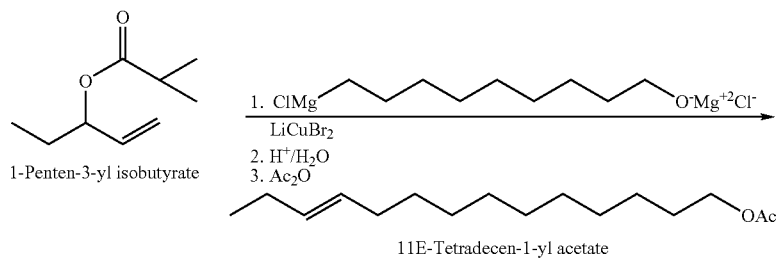

Preparation of 11E-Tetradecen-1-yl Acetate

A solution of methyl Grignard (MeMgCl, 187 mL, 3.1 M/THF, 0.589 mol) is added to a solution of 9-chloro-1-nonanol (100 g, 0.561 mol) in tetrahydrofuran (200 mL, 2.47 mol) at a rate that maintains the pot temperature below 50° C., cooling may be necessary. The mixture is then further stirred for 30 minutes.

Magnesium chips (14 g, 0.577 mol) are suspended in tetrahydrofuran (150 mL, 1.85 mol) and then heated to reflux (67-68° C.). The chloroalkoxide is fed dropwise and the mixture is refluxed further until the reaction is complete by GC/FID (~3-4 hours). The Grignard solution is then cooled and diluted, if needed, with tetrahydrofuran for the coupling in the next step.

The alkoxide Grignard solution is added to a mixture of 1-penten-3-yl isobutyrate ester (81.0 g, 0.517 mol) and LiCuBr$_2$ reagent (1 M/THF, 61.0 mL) at a rate that maintains the reaction temperature between 25-30° C., with cooling as necessary. The mixture is stirred for 15 minutes then quenched with aqueous citric acid solution (1 L). The layers are separated and the organic portion is washed with water (2×150 mL) and dilute sodium hydroxide solution (until pH basic). The organic portion is then stripped of solvent and the residue fed to acetic anhydride at 110° C. Upon reaction completion the mixture is washed with water (2×150 mL) and dilute sodium carbonate solution (until pH basic) then evaporated to afford crude monoene acetate, which is then purified by distillation (b.p. 115° C., 0.1 mm Hg) to collect 85.4 g of the desired acetate product in 65% overall yield for the two steps (E/Z 86:14, m/z 254).

EXAMPLE 2

Chlorononanal Diethylacetal Coupling to 1,4-Pentadien-3-yl Isobutyrate

Black Headed Budworm

11E,13-Tetradecadienal

Preparation of Chlorononanal Diethyl Acetal Grignard:

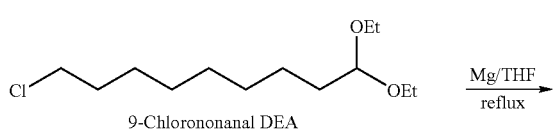

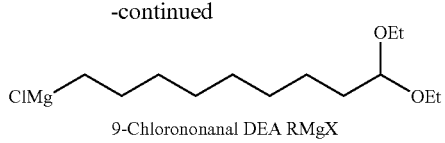

Preparation of 11E,13-Tetradecadienal Diethylacetal:

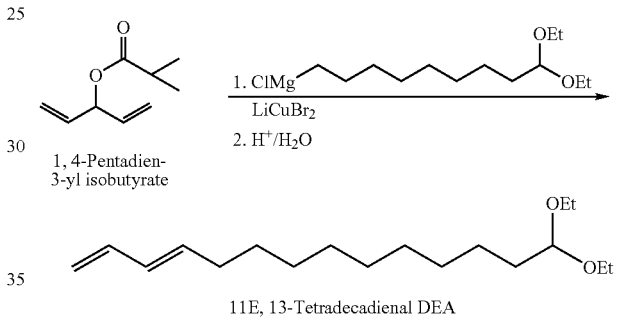

Preparation of 11E,13-Tetradecadienal:

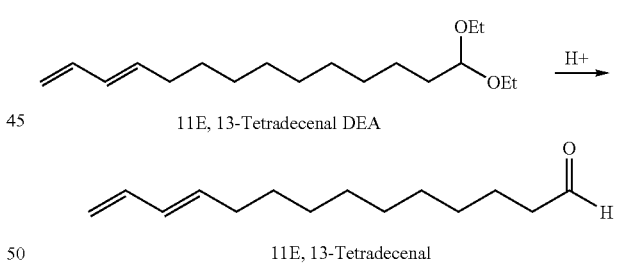

Preparation of 11E,13-Tetradecadienal

Magnesium chips (19.5 g, 0.800 mol) are suspended in tetrahydrofuran (170 mL) and then heated to reflux (67-68° C.). The chlorononanal DEA solution (200 g, 0.800 mol in 300 mL THF) is fed dropwise and the mixture is refluxed further until the reaction is complete by GC/FID (~3-4 hours). The Grignard solution is then cooled and diluted, if needed, with tetrahydrofuran for the coupling in the next step.

The Grignard solution is then added to a mixture of 1,4-pentadien-3-yl isobutyrate ester (114 g, 0.740 mol) and LiCuBr$_2$ reagent (1 M/THF, 86 mL) at a rate that maintains the reaction temperature between 25-30° C., with cooling as necessary. The mixture is stirred for 15 minutes then quenched with aqueous citric acid solution (1 L). The layers are separated and the organic portion is washed with water (2×) and dilute sodium hydroxide solution (until pH basic). The crude organic portion is then stripped of solvent and distilled to afford 56.2 g of the 11,13-tetradecadienal DEA product (b.p. 150° C., 0.1 mm Hg, Yld. 27%, m/z 282), which is subsequently deprotected at room temperature with formic acid in heptane to give 11,13-tetradecadienal (40.0 g, Yld. 94%, E/Z 76:24).

EXAMPLE 3

Chloropropanol Coupling to 1-Hepten-3-yl Isobutyrate

Peach Twig Borer

5E-Decen-1-yl acetate

Preparation of Chloropropanol Alkoxide:

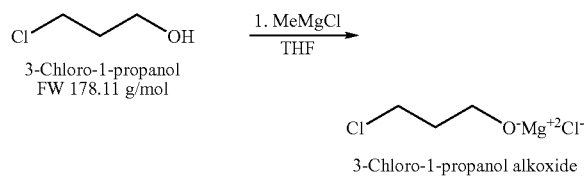

Preparation of Chloropropanol Alkoxide Grignard:

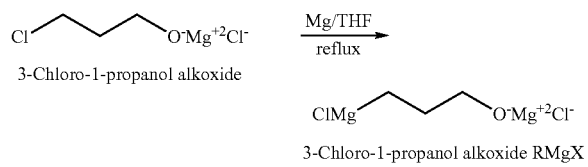

Preparation of 5E-Decen-1-yl Acetate

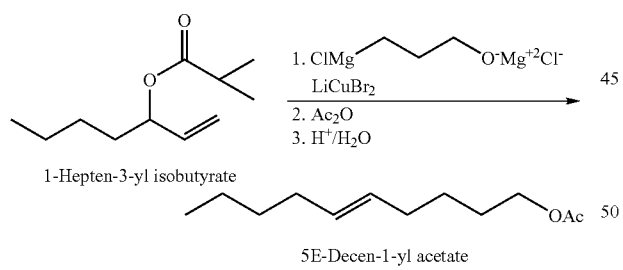

Preparation of 5E-Decen-1-yl Acetate

A solution of methyl Grignard (MeMgCl, 1.53 L, 3.1 M/THF, 4.86 mol) is added to a solution of 3-chloro-1-propanol (441.0 g, 4.66 mol) in tetrahydrofuran (1.74 L, 21.38 mol) at a rate that maintains the pot temperature below 40° C., cooling may be necessary. The mixture is then further stirred for 30 minutes.

Magnesium chips (115.7 g, 4.76 mol) are suspended in tetrahydrofuran (1.74 L, 21.38 mol) and then heated to reflux (67-68° C.). The chloroalkoxide is fed dropwise and the mixture is refluxed further until the reaction is complete by GC/FID (~3-4 hours).

The alkoxide Grignard solution is added to a mixture of 1-hepten-3-yl isobutyrate ester (745.6 g, 4.05 mol) and LiCuBr₂ reagent (1 M/THF, 471.6 mL) at a rate that maintains the reaction temperature between 25-30° C., with cooling as necessary. The mixture is stirred for 15 minutes then quenched with aqueous citric acid solution. The layers are separated and the organic portion is washed with water (2×) and dilute sodium hydroxide solution (until pH basic). The organic portion is then stripped of solvent and the residue fed to acetic anhydride at 110° C. Upon reaction completion the mixture is washed with water (2×) and dilute sodium carbonate solution (until pH basic) then evaporated to afford crude monoene acetate (E/Z 87:13, m/z 198.3), which is then purified by distillation (b.p. 68° C., 0.1 mm Hg) to collect 601.8 g of the desired acetate product in 75% yield.

EXAMPLE 4

Chlorohexanol Coupling to 1,4E-Hexadien-3-yl Isobutyrate

Codlure 8E,10E-Dodecadien-1-ol

Preparation of Chlorohexanol Alkoxide:

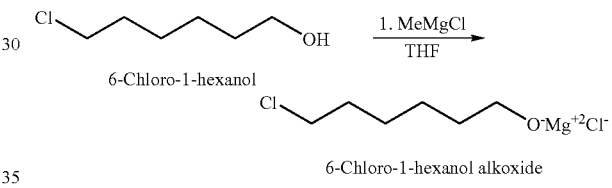

Preparation of Chlorohexanol Alkoxide Grignard:

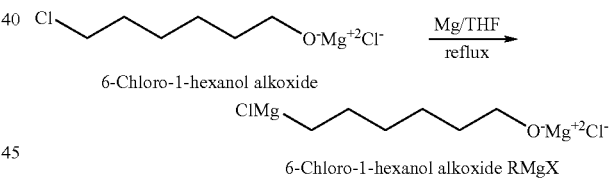

Preparation of 8E,10E-Dodecadien-1-ol

A solution of methyl Grignard (MeMgCl, 380 mL, 3.1 M/THF, 1.18 mol) is added to a solution of 6-chloro-1-hexanol (158 g, 1.16 mol) in tetrahydrofuran (499 mL, 4.94 mol) at a rate that maintains the pot temperature below 50° C., cooling may be necessary. The mixture is then further stirred for 30 minutes.

Magnesium chips (28 g, 1.15 mol) are suspended in tetrahydrofuran (300 mL, 3.70 mol) and then heated to reflux (67-68° C.). The chloroalkoxide is fed dropwise and the mixture is refluxed further until the reaction is complete by GC/FID (~3-4 hours). The Grignard solution is then cooled and diluted, if needed, with tetrahydrofuran for the coupling in the next step.

The alkoxide Grignard solution is added to a mixture of 1,4E-hexadien-3-yl isobutyrate ester (210 g, 1.25 mol) and LiCuBr₂ reagent (1 M/THF, 125 mL) at a rate that maintains the reaction temperature between 25-30° C., with cooling as necessary. The mixture is stirred for 15 minutes then quenched with aqueous citric acid solution (1 L). The layers are separated and the organic portion is washed with water (2×) and dilute sodium hydroxide solution (until pH basic). The organic portion is then stripped of solvent and distilled over a short column (b.p. 122° C., 0.1 mm Hg) to afford 115.5 g of the desired diene alcohol (70:30 8E,10E/8Z,10E) in 55% overall yield.

EXAMPLE 5

Chlorononanal Diethylacetal Coupling to 1-Penten-3-yl Isobutyrate

Spruce Budworm

11E-Tetradecenal

Preparation of Chlorononanal Diethyl Acetal Grignard:

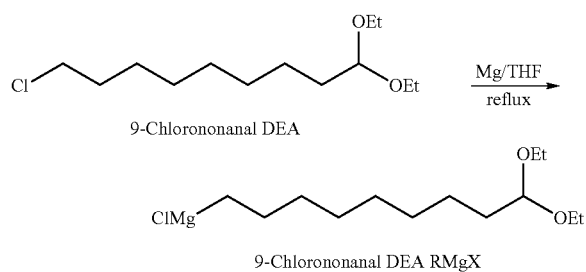

Preparation of 11E-Tetradecenal Diethylacetal:

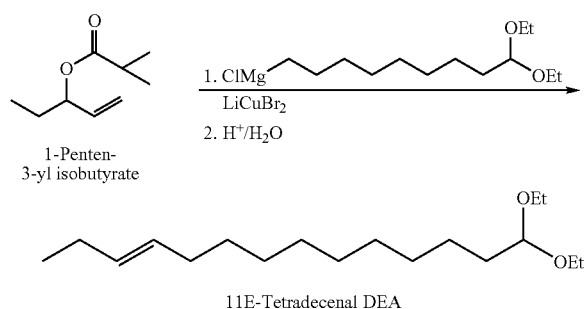

Preparation of 11E-Tetradecenal:

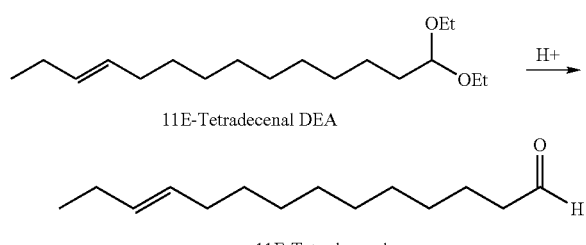

Preparation of 11E-Tetradecenal

Magnesium chips (14.7 g, 0.610 mol) are suspended in tetrahydrofuran (150 mL) and then heated to reflux (67-68° C.). The chlorononanal DEA solution (147 g, 0.586 mol in 400 mL THF) is fed dropwise and the mixture is refluxed further until the reaction is complete by GC/FID (~3-4 hours). The Grignard solution is then cooled and diluted, if needed, with tetrahydrofuran for the coupling in the next step.

The Grignard solution is then added to a mixture of 1-penten-3-yl isobutyrate ester (84 g, 0.538 mol) and LiCuBr$_2$ reagent (1 M/THF, 63 mL) at a rate that maintains the reaction temperature between 25-30° C., with cooling as necessary. The mixture is stirred for 15 minutes then quenched with aqueous citric acid solution (1 L). The layers are separated and the organic portion is washed with water (2×) and dilute sodium hydroxide solution (until pH basic). The crude organic portion is then stripped of solvent and distilled to afford 98.1 g of the 11E-tetradecenal DEA product (b.p. 150° C., 0.1 mm Hg, Yld. 64%, m/z 284), which is subsequently deprotected using formic acid in heptane at room temperature to give 11-tetradecenal (67.3 g, Yld. 67%, E/Z 83:17).

EXAMPLE 6

Chlorononanol THP Ether Coupling to 1-Penten-3-yl Isobutyrate

LBAM Monoene Component

11E-Tetradecen-1-yl acetate

Preparation of Chlorononanol THP Ether Grignard:

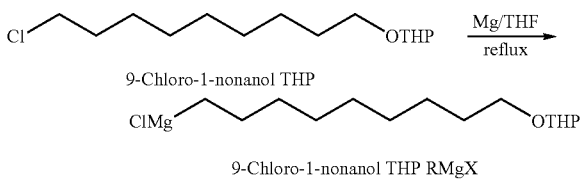

Preparation of 11E-Tetradecen-1-yl Acetate:

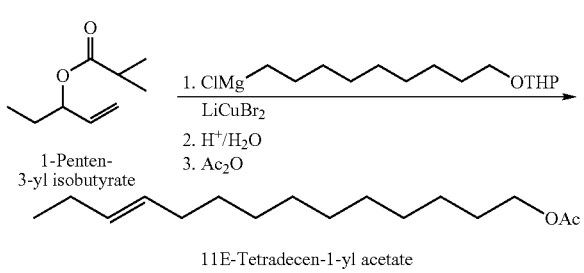

Preparation of 11E-Tetradecen-1-yl Acetate

Magnesium chips (19.1 g, 0.786 mol) are suspended in tetrahydrofuran (200 mL) and then heated to reflux (67-68° C.). A solution of 9-chlorononan-1-yl tetrahydropyranyl ether (199 g, 0.757 mol in 300 mL THF) is then fed dropwise and the mixture is refluxed further until the reaction is complete by GC/FID (~3-4 hours). The Grignard solution is then cooled and diluted, if needed, with tetrahydrofuran for the coupling in the next step.

The Grignard solution is then added to a mixture of 1-penten-3-yl isobutyrate ester (109 g, 0.698 mol) and LiCuBr$_2$ reagent (1 M/THF, 82 mL) at a rate that maintains the reaction temperature between 25-30° C., with cooling as necessary. The mixture is stirred for 15 minutes then quenched with aqueous citric acid solution (1 L). The layers are separated and the organic portion is washed with water (2×) and dilute sodium hydroxide solution (until pH basic). The organic portion is then stripped of solvent and the residue is deprotected using p-TSA in MeOH at room temperature to afford the crude monoene alcohol, which is subsequently fed to acetic anhydride at 110° C. Upon reaction completion the mixture is washed with water (2×) and dilute sodium carbonate solution (until pH basic) then evaporated to afford crude monoene acetate, which is then purified by distillation (b.p. 115° C., 0.1 mm Hg) to collect 113.5 g of the desired acetate product in 64% overall yield (E/Z 83:17, m/z 254).

EXAMPLE 7

Bromodioxolane Coupling to 1-Penten-3-yl Isobutyrate

Fragrance Application

5E-Octenal

Preparation of Bromodioxolane Grignard:

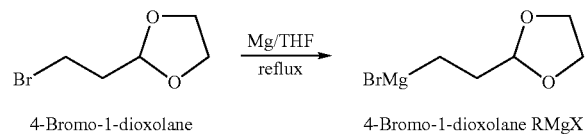

4-Bromo-1-dioxolane      4-Bromo-1-dioxolane RMgX

Preparation of 5E-Octen-1-yl Dioxolane:

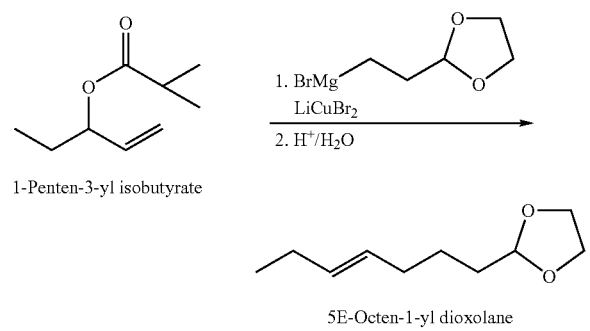

1-Penten-3-yl isobutyrate

5E-Octen-1-yl dioxolane

Preparation of 5E-Octenal:

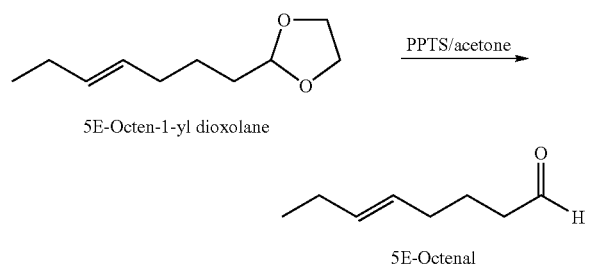

5E-Octen-1-yl dioxolane

5E-Octenal

Preparation of 5E-Octenal

Magnesium chips (1.4 g, 56.8 mmol) are suspended in tetrahydrofuran (15 mL) and a tetrahydrofuran solution of 2-(2-bromoethyl)-1,3-dioxolane (10 g, 55.2 mmol) is added dropwise at a rate that maintains the temperature between 25-30° C., with cooling as necessary. The mixture is allowed to stir 30 minutes further then set aside for the coupling in the next step.

The Grignard solution is added to a mixture of 1-penten-3-yl isobutyrate ester (7.98 g, 51.1 mmol) and LiCuBr$_2$ reagent (1 M/THF, 6.0 mL) at a rate that maintains the reaction temperature between 25-30° C., with cooling as necessary. The mixture is stirred for 15 minutes then quenched with aqueous citric acid solution (200 mL). The layers are separated and the organic portion is washed with water (2×) and dilute sodium hydroxide solution (until pH basic). The crude organic portion is then stripped of solvent to give 6.07 g monoene dioxolane product (m/z 171, E/Z 79:21 ratio, Yld 70%), which is then subsequently deprotected using PPTS (pyridinium p-toluenesulfonate) in refluxing acetone to afford 5E-octenal.

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

We claim:

1. A process for preparation of a compound of the formula (I)

wherein R$_2$ is selected from the group consisting of a branched or unbranched, saturated, ethylenically mono or di unsaturated aliphatic radical, Z is selected from the group consisting of —CH$_2$OH, —CH$_2$OAc or —CHO, m is a whole positive integer of one or more, and Ac is an acetyl group wherein the process comprises reacting a substituted and unsubstituted 1-alken-3-yl alkylate compound of the formula (II)

wherein R$_2$ is selected from the group consisting of a branched or unbranched, saturated, ethylenically mono or di unsaturated aliphatic radical, and R$_3$ is branched or unbranched alkyl group of 2 or more carbon atoms, with a halo alkanol Grignard reagent of the formula (III)

$$X-(Mg)_n-(CH_2)m-Y \quad\quad (III)$$

in the presence of a catalyst, wherein X is a halogen selected from the group consisting of Cl, Br and I, n is 1, m is a whole positive integer of 1 or more, and Y is selected from the group consisting of —O—Mg$^{+2}$X$^-$, or (—OR$_4$)$_2$ and

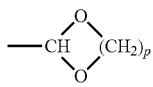

wherein $R_4$ is an alkyl group of from 1 to 4 carbon atoms and p is a whole integer of from 1 to 4 and with the proviso that when Y is $(-OR_4)_2$ or

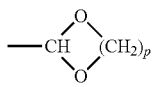

m is 1 or more to produce a compound of formula (I) wherein Z is $-CH_2OH$, and when a product of formula (I) wherein Z is $CH_2OAc$ is desired the product of formula (I) wherein Z is $CH_2OH$ is reacted with an acetylating agent, and when a product of formula (I) wherein Z is CHO is desired the reactant of formula (III) wherein Y is $(-OR_4)_2$ or

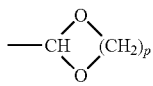

is employed and the resulting reaction product is deprotected to provide the aldehyde (—CHO) group.

2. The process of claim 1 wherein the reaction of reactants (II) and (III) is conducted in the presence of a copper catalyst.

3. The process of claim 2 wherein the reaction of reactants (II) and (III) is conducted in the presence of a lithium copper halide catalyst $LiCu(X^2)_2$ wherein $X^2$ is chlorine, bromine or iodine.

4. The process of claim 2 wherein a bromine is present in either the reactant of formula (III) or in the lithium copper halide catalyst.

5. The process of claim 3 wherein a bromine is present in either the reactant of the formula (III) or in the lithium copper halide catalyst.

6. The process of claim 2 wherein $R_2$ is an ethylenically unsaturated aliphatic radical.

7. The process of claim 2 wherein the product of formula (I) produced by the process is selected from the group consisting of dodecanyl acetate, 7E-dodecenyl acetate, 8E-dodecenyl acetate, 9E-dodecenyl acetate, 10E-dodecenyl acetate, 11-dodecenyl acetate, 9E,11-dodecadienyl acetate, 11E-tridecenyl acetate, tetradecanyl acetate, 7E-tetradecenyl acetate, 8E-tetradecenyl acetate, 9E-tetradecenyl acetate, 10E-tetradecenyl acetate, 11 E-tetradecenyl acetate, 12E-pentadecenyl acetate, hexadecanyl acetate, 11E-hexadecenyl acetate, octadecanyl acetate, 7E,9Z-dodecadienyl acetate, 7E,9E-dodecadienyl acetate, 8E,10E-dodecadienyl acetate, 9E,12Z-dodecadienyl acetate, 4E,7Z-tridecadienyl acetate, 9E,11E-tetradecadienyl acetate, 7E,11Z-hexadecadienyl acetate, 7E, 11E-hexadecadienyl acetate, 3E,13Z-octadecadienyl acetate, 3E,13E-octadecadienyl acetate, 6E-nonenol, dodecanol, 11-dodecenol, 7E-dodecenol, 8E-dodecenol, 9E-dodecenol, 9E,11-dodecadienol, 5E,7E-dodecadienol, 8E,10E-dodecadien-1-ol (codlemone, codlure), 8E,10Z-dodecadienol, 7E,9Z-dodecadienol, 5E-tetradecenol, 9E-tetradecenol, 11 E-tetradecenol, 14E-methyl-8-hexadecen-1-ol, 10E, 12E-hexadecadienol, 10E,12Z-hexadecadienol, dodecanal, tetradecanal, 11 E-tetradecenal, 11E,13-tetradecadienal, 8E,10E-tetradecadienal, hexadecanal, 10E-hexadecenal, 11 E-hexadecenal, 14E-14-methyl-8-hexadecenal, 10E, 12E-hexadecadienal, 10E,12Z-hexadecadienal, octadecanal and 13E-octadecenal.

8. A process according to claim 7 wherein the product of formula (I) produced by the process is selected from the group consisting of 11E-tetradecen-1-yl acetate, 11 E, 13-tetradecadienal, 5E-decen-1-yl acetate, 8E, 10E-dodecadien-1-ol, 11E-tetradecenal, and 5E-octenal.

9. A process according to claim 1 wherein $R_3$ of the reactant of formula (II) is a $C_3$ alkyl group.

10. A process according to claim 3 wherein $R_3$ of the reactant of formula (II) is a $C_3$ alkyl group.

11. A process according to claim 4 wherein $R_3$ of the reactant of formula (II) is a $C_3$ alkyl group.

12. A process according to claim 5 wherein $R_3$ of the reactant of formula (II) is a $C_3$ alkyl group.

13. A process according to claim 2 wherein the catalyst is present in a mole percent of 4 or more based on the halo alkanol Grignard reagent of formula (III).

14. A process according to claim 3 wherein the catalyst is present in a mole percent of 4 or more based on the halo alkanol Grignard reagent of formula (III).

15. A process according to claim 4 wherein the catalyst is present in a mole percent of 4 or more based on the halo alkanol Grignard reagent of formula (III).

16. A process according to claim 5 wherein the catalyst is present in a mole percent of 4 or more based on the halo alkanol Grignard reagent of formula (III).

17. The process of claim 1 wherein m is a numeral of from 1 to 4.

18. A process according to claim 1 wherein the reaction is conducted at a temperature of from about 20° C. to about 45° C.

19. A reaction according to claim 1 wherein the reaction is conducted by adding reactant (III) to a reaction vessel containing reactant (II) and the catalyst.

20. A reaction according to claim 1 wherein a lithium copper halide catalyst $LiCu(X^2)_2$ wherein $X^2$ is chlorine, bromine or iodine is employed and the catalyst is present in a mole percent of 4 or more based on the halo alkanol Grignard reagent of formula (III), bromine is present in either the reactant of formula (III) or in the lithium copper halide catalyst, and $R_2$ is an ethylenically unsaturated aliphatic radical.

* * * * *